United States Patent [19]

Abthoff et al.

[11] Patent Number: 4,691,562
[45] Date of Patent: Sep. 8, 1987

[54] PROCESS FOR DETERMINING AGING CONDITION OF EXHAUST-GAS CATALYST

[75] Inventors: Joerg Abthoff, Pluederhausen; Hans D. Schuster, Schorndorf; Hans J. Langer, Remseck; Wolfgang Zahn, Stuttgart; Günther Ebinger, Heiningen, all of Fed. Rep. of Germany

[73] Assignee: Daimler-Benz Aktiengesellschaft, Fed. Rep. of Germany

[21] Appl. No.: 890,540

[22] Filed: Jul. 30, 1986

[30] Foreign Application Priority Data

Jul. 30, 1985 [DE] Fed. Rep. of Germany ....... 3527175

[51] Int. Cl.⁴ ........................................... G01M 19/00
[52] U.S. Cl. ................................................. 73/118.1
[58] Field of Search .............................. 73/116, 118.1

[56] References Cited

U.S. PATENT DOCUMENTS

| | | | |
|---|---|---|---|
| 3,667,914 | 6/1972 | Penquite | 73/118.1 |
| 3,969,932 | 7/1976 | Rieger et al. | 73/118.1 |
| 4,116,053 | 9/1978 | Blanke | 73/117.3 |
| 4,175,427 | 11/1979 | Blanke | 73/118.1 |
| 4,315,243 | 2/1982 | Calvert, Sr. | 73/118.1 |

OTHER PUBLICATIONS

Proceedings International Symposium on Automotive Technology & Automation, Isata 81, Stockholm, Sep. 7-11, vol. 1, pp. 308-326, Automotive Automation Ltd, Croydon, England.

Primary Examiner—Stewart J. Levy
Assistant Examiner—Robert R. Raevis

[57] ABSTRACT

A process is described for the determination of the aging condition of an exhaust-gas catalyst for an internal combustion engine which is fitted with λ-controlled regulation of the fuel/air ratio. In the process, the switching of the fuel/air ratio from rich to lean and vice versa is delayed and the content of the combustibles in the exhaust gas downstream of the catalyst is measured. With delayed switching, complete conversion of the exhaust gas only occurs when the catalyst still possesses its full oxygen-storage capability. Since the oxygen-storage capability decreases with increasing age of the catalyst, the degree of conversion or the proportion of combustible components arising in the exhaust gas when conversion is no longer complete is a direct measure of the aging condition of the catalyst. A catalyst can thus be replaced in good time before it is completely destroyed and before undesired components of the exhaust gas reach the atmosphere.

9 Claims, 3 Drawing Figures

PROCESS FOR DETERMINING AGING CONDITION OF EXHAUST-GAS CATALYST

BACKGROUND AND SUMMARY OF THE INVENTION

The present invention relates to a process for the determination of the aging condition of an exhaust-gas catalyst for an internal combustion engine which is fitted with $\lambda$-controlled regulation of the fuel/air ratio.

The fulfillment of certain legal requirements for exhaust-gas composition can only be achieved by catalytic treatment of the exhaust gases. In order to ensure that the catalyst works optimally during normal driving operation, the fuel/air ratio must fluctuate between very tight limits about the stoichiometric ratio. This is accomplished by connecting a $\lambda$-probe system in front of the catalyst, the system being used to determine the residual oxygen in the exhaust gas.

Conclusions on the fuel/air ratio are drawn from the voltage (EMF) produced by the $\lambda$-probe via a probe line. The desired $\lambda$-control point is set via adjustable electronic parameters, such as threshold value, operating point, integrator characteristics and retardation times. On the basis of the characteristic curve of the probe, the regulator connected to the probe generally works as a two-position controller, such that the proportion of fuel in the fuel/air mixture is increased or decreased when the voltage produced deviates from the operating point. Due to the gas transit times in the engine, a constant oscillation between a rich and a lean fuel/air mixture is thereby produced.

It is known that the catalysts react relatively sensitively to overheating and, in particular, to impurities and additives, lead compounds for example, in the fuel. In addition, a certain amount of aging of the catalysts occurs under the hard operating conditions in a vehicle. All the factors mentioned above lead to a reduction in performance of the catalyst.

As soon as the reduction in performance of the catalyst has reached a certain level, the catalyst should be replaced. If at all possible, this should be done before the catalyst is so badly destroyed that its non-operative condition can even be observed externally. Thus, a simple process for testing the aging condition of a catalyst in a combustion engine is desirable.

One of the objects of the present invention is to provide a simple process which can be carried out in practically any motor vehicle workshop to determine the aging condition of the catalyst.

These and other objects are achieved in a process for measuring the aging condition of a catalyst for an internal combustion engine that has $\lambda$-controlled regulation of the fuel/air ratio that is switched from rich to lean and lean to rich, by providing the delaying of the switching of the fuel/air ratio, and measuring the amount of combustible components in the exhaust gas after it has passed the catalyst.

Further objects, features and advantages of the present invention will become more apparent from the following description when taken with the accompanying drawings, which show for purpose of illustration only, an embodiment constructed in accordance with the present invention.

DETAILED DESCRIPTION OF THE INVENTION

Figure 1A:
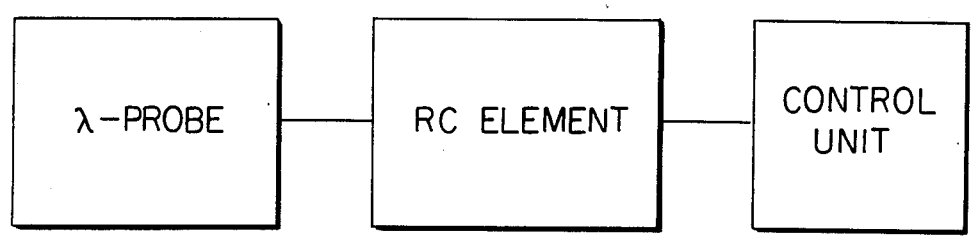
FIG. 1a is a schematic view of the preferred embodiment of FIG. 1 with an RC element as the delay element.
Figure 1B:
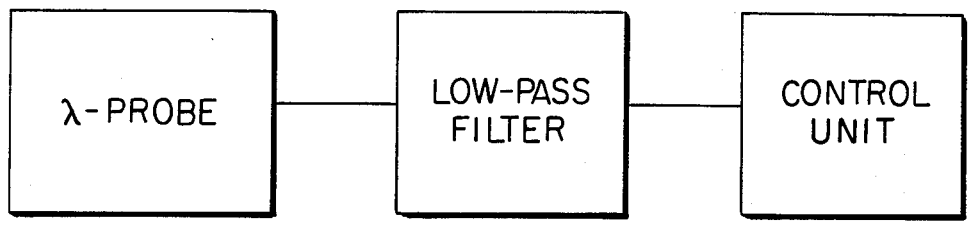
FIG. 1b is a schematic view of the preferred embodiment of FIG. 1 with a low pass filter element as the delay element.

The present invention uses the fact that the catalyst is able to store oxygen on combustion of a lean mixture ($\lambda > 1$, excess of oxygen in the exhaust gas), and the combustible components still in the exhaust gas can be oxidized by this oxygen on combustion of a rich mixture ($\lambda < 1$, deficiency of oxygen in the exhaust gas). A catalyst with full catalytic activity has a relatively large capacity for oxygen storage. In the course of the aging process of the catalyst, however, the capacity to store oxygen, and thus also the activity of the catalyst, decreases.

Because of the functioning of the $\lambda$-controlled regulation of the fuel/air ratio, this ratio oscillates between rich and lean with a certain frequency during normal operation. The mode of operation of $\lambda$-controlled regulation is generally known and is, for example, described in detail in: Glockler, "Advances in closed-loop lambda-controlled fuel injection systems. Means to meet most stringent emission levels", Proceedings International Symposium on Automotive Technology & Automation, ISATA 81, Stockholm Sept. 7–11, volume 1, pages 308–326, published by Automotive Automation Ltd., Croydon, England.

If the switch from a rich to a lean mixture or vice versa is retarded or delayed by a certain period of time in order to test the catalyst, then both the time in which the catalyst is presented with a gas having a deficiency of oxygen and also the time in which an exhaust gas with an excess of oxygen is presented, will be extended. The exhaust gas, still containing oxidizable components, and being deficient of oxygen, can only be completely oxidized when the amount of oxygen stored in the catalyst during the oxygen excess phase is adequate for this. However, since the oxygen storage capacity of the catalyst decreases with decreasing age, so that the effectiveness of the catalyst is decreased, the proportion of combustible components in the exhaust gas which are no longer being converted is a measure of the oxygen storage capacity of the catalyst. This, in turn, is a measure of the catalyst's aging condition when the retardation of the changeover points is suitable selected. The degree of exhaustion of the catalyst can thus be determined from the amount of combustible components contained in the exhaust gas after the catalyst and the catalyst can, if necessary, be replaced before undesired exhaust-gas components reach the atmosphere, even in normal operation.

The amount of combustible components contained in the exhaust gas when the switching is delayed can be measured by any repair shop using the measuring equipment (CO measurement) in common use today, particularly when the engine is at idling speed or at a fast idle. Measurements to determine the CO content in the exhaust gas are, of course, already carried out today during the adjustment of carburetors.

The time by which the changeover is retarded or delayed when the normal switching point is reached is between 10 and 5000 msec., and in especially preferred embodiments, between 50 and 200 msec. The optimum retardation or delay time must be determined individually for different types of engines. For this purpose, the guide values which follow can serve as the starting point. If the volume of catalyst is large, the delay must also be relatively large, since a large volume of catalyst also has a large oxygen storage capacity. If the delay of the switching were too small, then the desired overloading of the catalyst would not occur, and the limit of the oxygen storage capacity could only be determined just before breakdown of the catalyst. Vehicles are frequently also provided with a mini-catalyst or start catalyst located very close to the exhaust system. Such a catalyst is located before the $\lambda$-probe and the actual catalyst in the exhaust-gas stream and has the job of warming up very quickly in the start-up phase and thereby reduce the amount of undesired components contained in the exhaust gas in the start-up phase. If such a catalyst is built in, then a reduction of the retardation time is appropriate since the exhaust gases reach the actual catalyst in an already partially converted condition.

Figure 1:
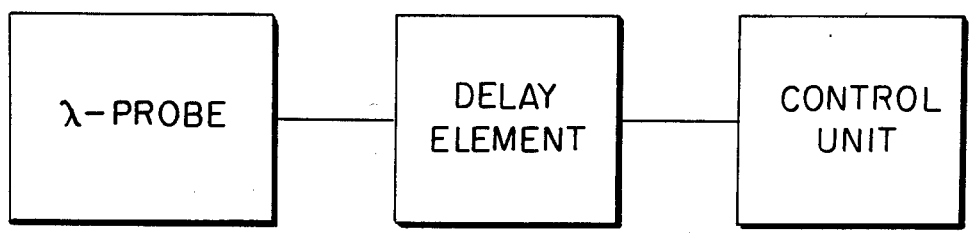
FIG. 1 is a schematic view of a preferred embodiment of a delaying device.

The changeover from rich to lean or vice versa can be delayed particularly simply in preferred embodiments by connection of a delay element such as an RC element or a low-pass filter in the line between the $\lambda$-probe and the control unit. This is illustrated in FIG. 1. In some contemplated embodiments, it is sufficient to bridge the plus and minus lines of the connection between the probe and the control unit using a condenser of suitable capacitance. If the delay is introduced by an RC element or a condenser connected in the line between the $\lambda$-probe and the control unit, then the practical execution of the invention is particularly simple, since the connection between the cable of the $\lambda$-probe and the control unit is a plug contact. If a suitable attachment plug containing the RC element or the condenser is now connected between the plug of the line and the plug contact of the control unit, then this can be carried out in a workshop without difficulty. The workshop needs only a set of suitable attachment plugs which are matched to the types of vehicle serviced by it.

Another contemplated embodiment for carrying out the delay is an appropriate delay element built into the control unit which is activated by using a switch when the catalytic converter is inspected. This type of solution has the advantage that no further equipment is necessary in the workshop, apart from the instruments for measuring the exhaust-gas composition that are available anyway.

The present invention measures the aging condition of the exhaust-gas catalyst in a vehicle in an exceptionally simple and elegant fashion. The equipment necessary for this is uncomplicated and most of it is already present in every motor vehicle workshop. The process has made it possible to recognize an exhausted catalyst, before it has become so unusable that undesired exhaust gases pass into the atmosphere during operation of the engine.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A process for the determination of the condition of an exhaust-gas catalyst for an internal combustion engine which is fitted with $\lambda$-controlled regulation of the fuel/air ratio, in which process, when the fuel/air ratio exceeds or falls below a pre-specified value, the fuel/air ratio is changed over from rich to lean or from lean to rich respectively, depending on the voltage produced by a $\lambda$-probe on reaching a changeover point, wherein the changeover is delayed by 10 to 5000 msec and the relative amount of combustible components arising in a exhaust gas after the exhaust gas has passed the catalyst is measured.

2. The process according to claim 1, wherein the changeover is delayed by 50 to 200 msec.

3. The process according to claim 2, wherein the delay is created by insertion of either an RC element or a low-pass filter into a current circuit of the $\lambda$-probe.

4. A process for determining the condition of an exhaust-gas catalyst for an internal combustion engine which has a $\lambda$-probe for $\lambda$-controlled regulation of the fuel/air ratio, in which the fuel/air ratio is switched from rich to lean or from lean to rich when said ratio exceeds or falls below a pre-specified value, said process including the steps of delaying the switching of the fuel/air ratio, and measuring the relative amount of combustible components in the exhaust gas after the exhaust gas has passed the catalyst.

5. The process of claim 4, wherein the fuel/air ratio is switched in response to a voltage produced by the $\lambda$-probe upon reaching a changeover point.

6. The process of claim 5, wherein the switching is delayed by 10 to 5000 msec.

7. The process of claim 5, wherein the switching is delayed by 50 to 200 msec.

8. The process of claim 5, wherein a resistive-capacitive element inserted in a current circuit of the $\lambda$-probe is used to delay the switching of the fuel/air ratio.

9. The process of claim 5, wherein a low pass filter element inserted in a current circuit of the $\lambda$-probe is used to delay the switching of the fuel/air ratio.

* * * * *